United States Patent
Richardson

(10) Patent No.: US 7,804,079 B2
(45) Date of Patent: Sep. 28, 2010

(54) METHOD AND APPARATUS FOR USING IMPERFECTIONS AND IRREGULARITIES IN OPTICAL MEDIA FOR IDENTIFICATION PURPOSES

(75) Inventor: Ric B. Richardson, Irvine, CA (US)

(73) Assignee: Uniloc USA, Inc., Irvine, CA (US)

( * ) Notice: Subject to any disclaimer, the term of this patent is extended or adjusted under 35 U.S.C. 154(b) by 0 days.

(21) Appl. No.: 11/470,246

(22) Filed: Sep. 5, 2006

(65) Prior Publication Data

US 2007/0131880 A1   Jun. 14, 2007

Related U.S. Application Data

(60) Provisional application No. 60/713,928, filed on Sep. 2, 2005.

(51) Int. Cl.
*G01N 21/88* (2006.01)

(52) U.S. Cl. ............... 250/559.4; 356/429; 209/588

(58) Field of Classification Search ............ 250/559.4, 250/234–236, 562, 563, 571, 572, 559.45, 250/559.48, 559.59; 356/238, 239, 429–431, 356/237.2, 239.1, 237.1; 364/507; 209/588
See application file for complete search history.

(56) References Cited

U.S. PATENT DOCUMENTS

| | | | | |
|---|---|---|---|---|
| 5,414,269 A | * | 5/1995 | Takahashi | 250/559.4 |
| 5,974,150 A | * | 10/1999 | Kaish et al. | 713/179 |
| 6,294,793 B1 | * | 9/2001 | Brunfeld et al. | 250/559.45 |
| 2006/0072444 A1 | * | 4/2006 | Engel et al. | 369/275.1 |

* cited by examiner

*Primary Examiner*—Seung C Sohn
(74) *Attorney, Agent, or Firm*—Sean D. Burdick

(57) ABSTRACT

A method for using optical media for identification purpose including the steps of exposing a portion of the optical media to a source of radiation; detecting an imperfection in the portion of the optical media; and, quantifying the imperfection to create a unique identifier. An apparatus for using an optical media for identification purposes, including a light source for exposing a portion of the optical media to a radiation; and, a receptor for receiving the radiation through the portion of the optical media, wherein the receptor measures a change in radiation that is received once the radiation has passed through the portion of the optical media.

24 Claims, 2 Drawing Sheets

METHOD AND APPARATUS FOR USING IMPERFECTIONS AND IRREGULARITIES IN OPTICAL MEDIA FOR IDENTIFICATION PURPOSES

CLAIM OF PRIORITY UNDER 35 U.S.C. §119

The present Application for Patent claims priority to Provisional Application No. 60/713,928, entitled "Method for using imperfections and irregularities in optical media and optical fiber for identification purposes" filed Sep. 2, 2005, and assigned to the assignee hereof and hereby expressly incorporated by reference herein.

BACKGROUND

1. Field

The present invention relates generally to computer security applications, and more particularly, to a method and apparatus for using imperfections and irregularities in optical media for identification purposes.

2. Background

Optical media and optical fiber have become ideal mediums for storing and communicating digital data. In recent years a focus of both these applications has moved to working out ways to make such storage and communications secure. A basic component of any security system is authenticating not only the sender and receiver of secure communications or data, but also the devices that are used as part of the storage and communications process.

Methods for securing data and communications include the introduction of secure components that have had a unique identity intentionally embedded into the component. These are known in the art as dongles. Another approach is to embed a unique identifier into the component itself. An example of this in the art is using secure computing platforms where the main CPU features a hard coded serial number that cannot be changed or modified after manufacture. Another example which is also currently in the art is CD-ROM disk serialization where a unique number is permanently added or written to the disk for reference by the software as it runs from the same disk.

One disadvantage of the above approaches to digital security and authentication is that the intentional identification of a device, by the use of a manufactured identifier or serialization number, is a specific and easily traced means of identification. This means that attackers and or reverse engineers have a specific and quantifiable target to initiate an attack on the security system. The approach described by the invention allows a wide and diverse range of identifiers to be used to uniquely identify the protected optical media or piece of fiber. This in turn significantly complicates the initial stages of any attacking or tampering process in that there is no central and easily identifiable identification device or serial number to attack.

Another disadvantage is the cost of manufacturing and connecting manufactured identifiers to the medium to be protected or authenticated. Considerable effort and expense is usually associated with ensuring that the manufactured identifiers cannot be separated from the optical media or optical fiber. For example, much of the expenses is associated with the writing of software that verifies the presence of and authenticate the manufactured identifier.

It is desirable that the disadvantages identified above be addressed.

SUMMARY OF THE PREFERRED EMBODIMENTS

The present invention allows the use of imperfections and irregularities present in optical media as a way of uniquely identifying the optical media, thereby allowing the component itself to become an integral optical part of an authenticated security system that can protect the data being stored on or communicated by the component. The present invention will reduce the costs of adding security capabilities to optical media while simplifying and increasing the speed of the manufacturing process when secure optical media is desired. In general, the present invention is a method for using the minute imperfections or irregularities that occur in optical fiber or other optical media so as to use these as a unique identifier for the purposes of authentication.

In one preferred embodiment, the present invention is implemented in a method for using optical media for identification purpose including the steps of exposing a portion of the optical media to a source of radiation; detecting an imperfection in the portion of the optical media; and, quantifying the imperfection to create a unique identifier.

In another preferred embodiment, the present invention is implemented as an apparatus for using an optical media for identification purposes, including a light source for exposing a portion of the optical media to a radiation; and, a receptor for receiving the radiation through the portion of the optical media, wherein the receptor measures a change in radiation that is received once the radiation has passed through the portion of the optical media.

In yet another preferred embodiment, the present invention is implemented as an apparatus for using an optical media for identification purposes, including a processor and a memory coupled to the processor. The memory is configured to cause the processor to execute a method comprising exposing a portion of the optical media to a source of radiation; detecting an imperfection in the portion of the optical media; and, quantifying the imperfection to create a unique identifier.

Other objects, features and advantages will become apparent to those skilled in the art from the following detailed description. It is to be understood, however, that the detailed description and specific examples, while indicating exemplary embodiments, are given by way of illustration and not limitation. Many changes and modifications within the scope of the following description may be made without departing from the spirit thereof, and the description should be understood to include all such variations.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION

Manmade optical media contains minute imperfections and irregularities. These imperfections and irregularities are routinely measured to determine the quality assurance of the product before sale and or distribution. It is the design of this invention that these measurements of imperfections or media irregularities can be used to uniquely identify the particular piece of optical media or optical fiber so that it can be used as part of an authentication or security system. As described herein, the term optical media includes media that is readable through optical means, including compact disc (CD), CD read-only-memories (CD-ROMs), digital versatile discs (DVDs) and DVD read-only-memory (DVD-ROMs). In addition, optical media could also refer to such optical media as fiber optic materials, or optical fiber. All these types of media are to be considered to be under the purview of the present disclosure.

Figure 1:
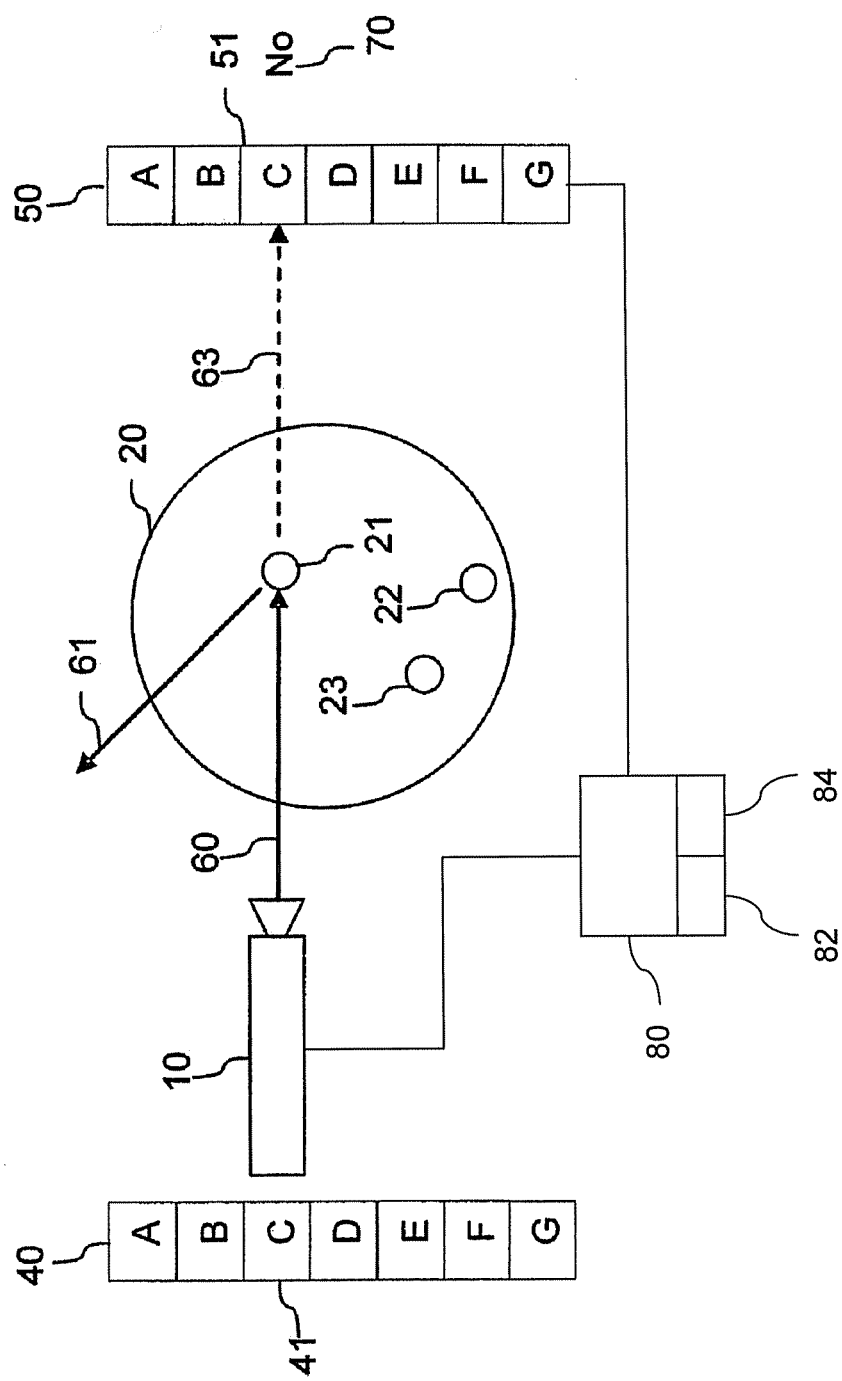
FIG. 1 illustrates an example of an optical identity verification system showing a negative reading.

FIG. 1 describes a method for using imperfections in an optical media for identification purposes, where a light 60 is transmitted through a piece of optical media 20. In one preferred embodiment, the light 60 is transmitted from a light source 10 at a particular location 41, which is one of a set of transmission locations, to a corresponding reception location 51, which is one of a set of reception locations.

After the light is transmitted from the light source 10, the light passes through the optical media 20. Optical media 20 contains a series of imperfections or irregularities 21, 22, 23. As the light 60 passes through the optical media 20, it may encounter a media irregularity 21 that reflects some or all of the light 61 so that a reduced level of light 63 or none at all passes through to the receptor 50 at the reception location 51. The result 70 of the amount of light received at the reception location 51 is then recorded for later computation.

One exemplary embodiment of an apparatus for implementing this invention comprises a laser transmitter 10, which directs the beam of light 60 through the media 20 to be uniquely identified. A laser receiver 50 measures the intensity of the received light 63 source, such as at the reception location "C" 51, after it has passed through the optical media 20. Due to the series of imperfections and irregularities 21, 22, 23 of the media itself, the recorded values 70, 71 of the received light 62, 63 will vary correspondingly based on the size and level of disruption caused by the series of imperfections or peculiarities 21, 22, 23 present in the media.

When these measurements are recorded for multiple locations 41, 51, 42, 52 within the target piece of optical media 20, the recorded values 70, 71 can be used to produce a unique identifier that, in turn, can be used to uniquely identify the individual piece of optical media for the purposes of identification and authentication.

Alternatively, light waves of other bandwidths and focus strengths other than those generated from laser may be used to sample the target optical media or optical fiber. The source of radiation can be a coherent light source or be a noncoherent light source.

In one preferred embodiment of the present invention, the original light source can come from a single light transmitter that moves from one location to the next during the sampling process or, alternatively, in another preferred embodiment of the present invention, multiple light transmitters in situ can be used to produce the sampling. The light receptor can be an analog or digital device.

Figure 2:
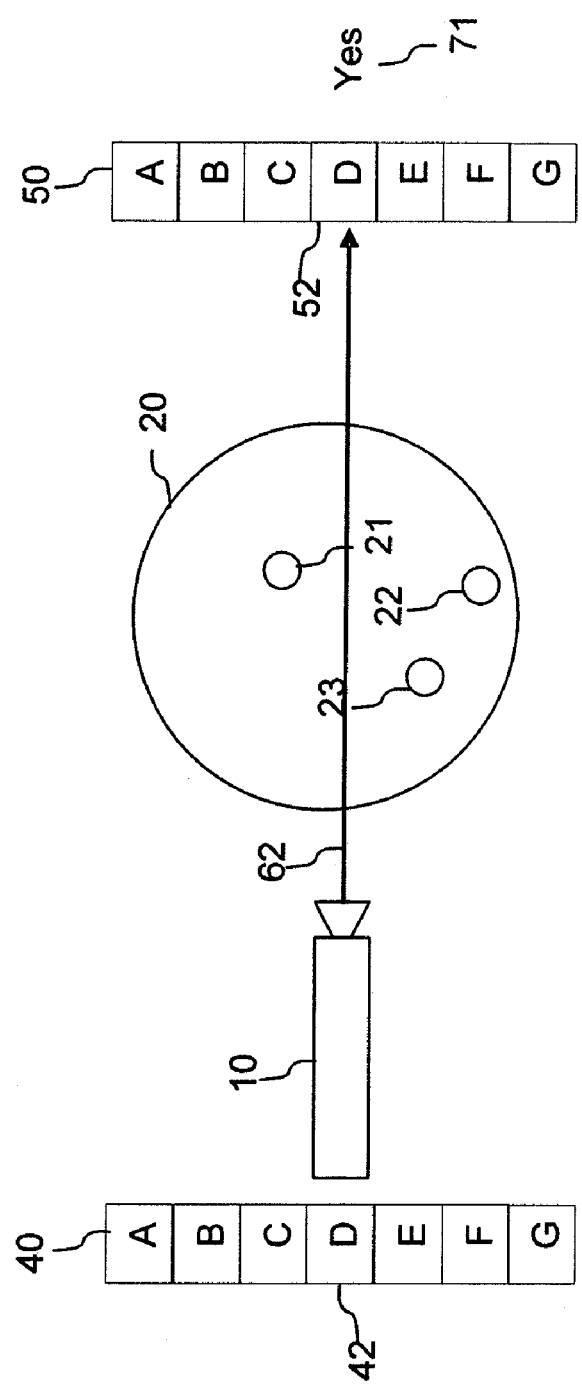
FIG. 2 illustrates an example of an optical identity verification system showing a positive reading.

FIG. 2 is similar to FIG. 1, except that it represents a situation where the light 62 is transmitted from light source 10 at a different location "D" 42 to a corresponding reception location 52. In this case, the light 62 does not encounter any reflective irregularities and the level of light recorded at the reception location 71 shows no reduction in intensity that would occur if the light had encountered an irregularity from the series of irregularities 21, 22, 23 while passing through the other portion media 20. Thus, in this case, a light intensity of one hundred is determined.

In one preferred embodiment of the present invention, the results of the light received from the light transmitter on the other side of the target media can be measured as a quantized value, namely, either on or off, or the results could be a measurement of light intensity, namely, one hundred for zero percent degradation or zero for one hundred percent degradation. A quantifier may be implemented as a part of a computer system 80 attached to the light transmitting apparatus (light source 10) and receiving apparatus (receiver 50). The computer system comprises a processor 82 and a memory 94. Different parts of the optical media may then be measured to generate the unique identifier. Thus, in the example as shown in FIGS. 1 and 2, seven positions or areas on media 20 may be measured and each may be quantified differently. For example, assuming sufficient disruption of light occurs at locations "C", "E" and "F" of the laser receiver 50 due to the series of imperfections 21, 22, 23 where a unique identifier generated as the identifier for optical media 20 is 1101001, where "1" represents a level of degradation that is not measurable or does not cross a threshold to cause the measurement to be classified as a disruption (e.g., 50% light intensity loss), and the "0" represents a level of degradation that crosses the threshold. In other preferred embodiments of the present invention, other variables such as frequency or phase shift of the light may be measured and quantified in addition to, or in lieu of, light intensity.

The embodiments described above are exemplary embodiments. Those skilled in the art may now make numerous uses of, and departures from, the above-described embodiments without departing from the inventive concepts disclosed herein. Various modifications to these embodiments may be readily apparent to those skilled in the art, and the generic principles defined herein may be applied to other embodiments, without departing from the spirit or scope of the novel aspects described herein. Thus, the scope of the invention is not intended to be limited to the embodiments shown herein but is to be accorded the widest scope consistent with the principles and novel features disclosed herein. The word "exemplary" is used exclusively herein to mean "serving as an example, instance, or illustration." Any embodiment described herein as "exemplary" is not necessarily to be construed as the most preferred or advantageous over other embodiments. Accordingly, the present invention is to be defined solely by the scope of the following claims.

What is claimed is:

1. A method for using optical media for identification purposes, comprising:

exposing a portion of the optical media to a source of radiation;

detecting one or more imperfections in the portion of the optical media;

quantifying the imperfections to create a unique identifier; and using the identifier as part of an authentication or security system to ensure that subsequent use of the optical media is properly authorized.

2. The method of claim 1 wherein the portion exposed to radiation comprises a number of different locations which may or may not include an imperfection, and wherein the unique identifier is generated as a result of the presence or lack of an imperfection at each different location.

3. The method of claim 1, wherein the source of radiation is a coherent light source.

4. The method of claim 1, wherein the source of radiation is a non-coherent light source.

5. The method of claim 1, wherein detecting the imperfection in the portion of the optical media comprises measuring a change of an intensity of the radiation after the radiation has passed though the portion of the optical media.

6. The method of claim 1, wherein detecting the imperfection in the portion of the optical media comprises measuring a change of a phase of the radiation after the radiation has passed though the portion of the optical media.

7. An apparatus for using an optical media for identification purposes, comprising:
   a light source for exposing a series of different locations of the optical media comprising one or more imperfections to a radiation;
   a receptor for receiving the radiation through the different locations of the optical media, wherein the receptor measures a change in radiation that is received once the radiation has passed through the different locations of the optical media comprising the imperfections;
   a computer system attached to the light source and to the receptor. the computer system configured to evaluate the change in the radiation received by the receptor and to determine from the evaluated change a unique identifier corresponding to the presence or lack of imperfections at the series of different locations;
   wherein the unique identifier is used to authenticate subsequent use of the optical media.

8. The apparatus of claim 7, wherein the unique identifier comprises a series of numbers consisting of 1s or 0s, wherein one of the 1 or 0 corresponds to the presence of an imperfection at one location, and the other of the 1 or 0 corresponds to the lack of an imperfection at one location on the optical media.

9. The apparatus of claim 7, wherein the source of radiation is a coherent light source.

10. The apparatus of claim 5, wherein the source of radiation is a non-coherent light source.

11. The apparatus of claim 7, wherein the evaluated change in radiation comprises a change of an intensity of the radiation after the radiation has passed though one of the different locations of the optical media.

12. The apparatus of claim 7, wherein the evaluated change in radiation comprises a change in phase of the radiation after the radiation has passed though one of the different locations of the optical media.

13. An apparatus for using optical media for identification purposes, comprising:
   a laser transmitter for directing a laser beam onto a series of different locations of an optical media;
   a laser receiver for receiving the laser beam after it has passed through the series of different locations of the optical media; and
   a processor configured to:
      evaluate the laser beam received by the laser receiver to detect a presence or lack of an imperfection at each location in the series of different locations,
      formulate a unique identifier for the optical media based on the detected presence or lack of an imperfection each location in the series of different locations, and
      record in a memory coupled to the processor the unique identifier to authenticate subsequent use of the optical media.

14. The apparatus of claim 13, wherein the unique identifier comprises a binary number, wherein one of a 1 or 0 corresponds to the presence of an imperfection at one location, and another of the 1 or 0 corresponds to the lack of an imperfection at one location on the optical media.

15. The apparatus of claim 13, wherein the source of radiation is a coherent light source.

16. The apparatus of claim 13, wherein the source of radiation is a non-coherent light source.

17. The apparatus of claim 13, wherein detecting the presence of the imperfection at each location of the optical media comprises measuring a change of an intensity of the radiation after the radiation has passed though each location of the optical media.

18. The apparatus of claim 13, wherein detecting the presence of the imperfection at each location of the optical media comprises measuring a change of a phase of the radiation after the radiation has passed though each location of the optical media.

19. The apparatus as recited in claim 7 wherein the evaluated change is a change in the intensity of the radiation.

20. The apparatus as recited in claim 7 wherein the evaluated change is a change in the phase of the radiation.

21. A method for uniquely identifying an optical media comprising the steps of:
   directing radiation to a first portion of the optical media;
   receiving the radiation once it has contacted the first portion of the optical media;
   evaluating a change in the radiation after it has contacted one or more imperfections existing in the first portion of the optical media;
   directing radiation to a second portion of the optical media;
   receiving the radiation once it has contacted the second portion of the optical media;
   evaluating a change in the radiation after it has contacted one or more imperfections existing in the second portion of the optical media;
   developing a unique identifier for the optical media based on the evaluated changes, wherein the unique identifier corresponds to the presence or lack of imperfections in the first and second portions; and
   storing and using the unique identifier to authenticate subsequent use of the optical media.

22. The method as recited in claim 21 wherein steps for directing radiation to the first portion and to the second portion of the optical media are performed using a common light source.

23. The method as recited in claim 21 further comprising additional sequences of directing, receiving, and evaluating steps in corresponding additional portions of the optical media, and wherein the unique identifier corresponds to the presence or lack of imperfections in all evaluated portions of the optical media.

24. The method as recited in claim 21 wherein the unique identifier comprises a binary number, wherein one of a 1 or 0 corresponds to the presence of an imperfection at one location, and another of the 1 or 0 corresponds to the lack of an imperfection at one location on the optical media.

* * * * *